United States Patent
Kim et al.

(10) Patent No.: US 7,347,970 B2
(45) Date of Patent: Mar. 25, 2008

(54) BIOCIDES BASED ON SILANOL TERMINATED SILANES AND SILOXANES

(75) Inventors: Yun Mi Kim, Gainesville, FL (US); Ronald H. Baney, Gainesville, FL (US); Anthony B. Brennan, Gainesville, FL (US)

(73) Assignee: University of Florida Research Foundation, Inc., Gainsville, FL (US)

( * ) Notice: Subject to any disclaimer, the term of this patent is extended or adjusted under 35 U.S.C. 154(b) by 451 days.

(21) Appl. No.: 11/057,611

(22) Filed: Feb. 14, 2005

(65) Prior Publication Data
US 2006/0194764 A1 Aug. 31, 2006

Related U.S. Application Data

(60) Provisional application No. 60/544,443, filed on Feb. 13, 2004.

(51) Int. Cl.
- *C07F 7/04* (2006.01)
- *A61L 2/00* (2006.01)
- *A61L 9/00* (2006.01)
- *A61L 2/18* (2006.01)

(52) U.S. Cl. ......................... 422/28; 556/440
(58) Field of Classification Search .............. 556/440; 422/28
See application file for complete search history.

(56) References Cited

U.S. PATENT DOCUMENTS

| 5,585,407 | A | 12/1996 | Patel et al. |
| 6,291,549 | B1 | 9/2001 | Mechtel et al. |
| 6,318,124 | B1 * | 11/2001 | Rutherford et al. ......... 65/60.8 |
| 2003/0008522 | A1 * | 1/2003 | Endisch et al. ........... 438/758 |
| 2003/0139619 | A1 * | 7/2003 | Nishiwaki et al. ......... 556/440 |

FOREIGN PATENT DOCUMENTS

| EP | 0857770 A | 8/1998 |
| WO | WO 2004/045552 | * 6/2004 |

OTHER PUBLICATIONS

Gravier et al. "A Review of the Fate and Effects of Silicones in the Environment", Journal of Polymers and the Environments, vol. 11, No. 4, Oct. 2003, pp. 129-136.

Bennett et al. "Primate Absorption and Elimination Balance Studies Including Pulmonary, Urinary, Biliary and Fecal Excretion of T-Butanol, Trimethylsilanol, Dimethylsilanediol and Hexamethyldisiloxane" Toxicology and Applied Pharmacology, 1973, 25(3):445.

* cited by examiner

*Primary Examiner*—Walter D. Griffin
*Assistant Examiner*—Lydia Edwards
(74) *Attorney, Agent, or Firm*—Akerman Senterfitt; Gregory A. Nelson; Gregory M. Lefkowitz

(57) ABSTRACT

A method of destroying target microorganisms comprises the step of contacting at least one target microorganism with at least one low molecular weight silanol end group containing molecule. The silanol containing molecule is selected from silanols ($R_1R_2R_3SiOH$), siloxanediols $HO(R_1R_2SiO)nH$ or siloxanols $HO(R_1R_2SiO)nSiR_1R_2R_3$, where $R_1$, $R_2$ and $R_3$ are selected from 1 to 4 carbon alkyl or fluoroalkyl moieties, or vinyl, or aryl groups and n is <6. The silanol end group containing molecule can be triethylsilanol, diphenylmethylsilanol, t-butyldimethylsilanol, n-butyldimethylsilanol, n-propyldimethylsilanol, ethyldimethylsilanol, vinylphenylmethylsilanol, phenyldimethylsilanol, 3,3,3 trifluoro propyldimethylsilanol, benzyldimethylsilanol and phenethyldimethylsilanol, or mixtures thereof. A composition of matter includes a silanol end group containing molecule according to the invention blended with a polymer or dissolved in aqueous solution along with an ether-based cosolvent.

19 Claims, 6 Drawing Sheets

BIOCIDES BASED ON SILANOL TERMINATED SILANES AND SILOXANES

CROSS-REFERENCE TO RELATED APPLICATIONS

This application claims the benefit of U.S. Provisional Patent Application No. 60/544,443 entitled "BIOCIDES BASED ON SILANOL TERMINATED SILANES" filed on Feb. 13, 2004, the entirety of which is incorporated herein by reference.

STATEMENT REGARDING FEDERALLY SPONSORED RESEARCH OR DEVELOPMENT

The Government has certain rights to the invention based on Office of Naval Research (ONR) Grant No. N00014-02-1-0325.

FIELD OF THE INVENTION

The invention related to biocides based on silanol terminated silanes and siloxanes.

BACKGROUND

There are a variety of applications that utilize biocides. Biofouling is one example. Biofouling is the result of marine organisms settling, attaching, and growing on submerged marine surfaces. The biofouling process is initiated within minutes of a surface being submerged in a marine environment by the absorption of dissolved organic materials which result in the formation of a conditioning film. Once the conditioning film is deposited, bacteria (unicellular algae) colonize the surface within hours of submersion. The resulting biofilm produced from the colonization of the bacteria is referred to as microfouling or slime and can reach thicknesses on the order of 500 μm.

Biofouling is estimated to cost the U.S. Navy alone over $1 billion per year by increasing the hydrodynamic drag of naval vessels. This in turn decreases range, speed, and maneuverability of naval vessels and increases the fuel consumption by up to 30-40%. Thus, biofouling weakens the national defense.

Any substrate in regular contact with water is likely to become fouled. No surface has been found that is completely resistant to fouling. Due to the vast variety of marine organisms that form biofilms, the development of a single surface coating with fixed surface properties for the prevention biofilm formation for all relevant marine organisms is a difficult if not impossible task.

Anti-fouling and foul-release coatings are two main approaches currently used for combating biofilm formation. Anti-fouling coatings prevent or deter the settling of biofouling organisms on a surface by the use of leached biocides, typically cuprous oxide or tributyltin, into the water. The biocides are either tethered to the coated surface or are released from the surface into the surrounding environment. Use of these types of coatings has caused damage to the marine ecosystem, especially in shallow bays and harbors, where the biocides can accumulate. As such, the use of tributyltin has been banned in many parts of the world. These products are effective for approximately 2 to 5 years.

Foul release coatings present a hydrophobic, low surface energy, and resulting slippery surface that minimizes the adhesion of the biofouling organisms. The most commonly used and highly successful of these is a nontoxic silicone-based paint. The silicone-based coating requires several layers to make it effective, and therefore it can be quite costly. Effectiveness lasts up to 5 years at which time recoating may become necessary. These products are considered to be more environmentally sound as compared to anti-fouling coatings because they do not leach toxins. However, they are subject to abrasion, and therefore their use is limited to areas that are not susceptible to damage caused by ice or debris.

Another application for biocides is for microbial decontamination. Bioterrorism puts military personnel as well as the general population at risk. Conventional types of biocides used in antiseptics and disinfectants inhibit or destroy only limited forms of bacteria and or other microorganisms. These antimicrobial materials usually are prepared from quaternary ammonium compounds with at least one of the organic groups attached to nitrogen being a long chain alkyl group. This class of antimicrobial materials undesirably generally lingers for a long period of time and can be environmentally harmful.

SUMMARY

A method of destroying target microorganisms comprises the step of contacting at least one target microorganism with at least one low molecular weight silanol end group containing molecule. The low molecular weight silanol containing molecule can comprise silanols ($R_1R_2R_3SiOH$), siloxanediols $HO(R_1R_2SiO)nH$ or siloxanols $HO(R_1R_2SiO)nSiR_1R_2R_3$, where $R_1$, $R_2$ and $R_3$ are selected from 1 to 4 carbon alkyl or fluoroalkyl moieties, or vinyl, or aryl groups and n is <6. Such silanol containing molecules have been found to be powerful antimicrobial agents, and are generally environmentally friendly and affordable agents.

The silanol end group containing molecule preferably comprises a low molecular weight silanol as defined above. For example, the silanol can comprise triethylsilanol, diphenylmethylsilanol, t-butyldimethylsilanol, n-butyldimethylsilanol, n-propyldimethylsilanol, ethyldimethylsilanol, vinylphenylmethylsilanol, phenyldimethylsilanol, 3,3,3-trifluoro propyldimethylsilanol, benzyldimethylsilanol or phenethyldimethylsilanol (also known as phenylethyldimethylsilanol), or mixtures thereof. The silanol can be disposed in an aqueous solution, where the solution preferably includes at least one ether cosolvent. The ether can comprise propylene glycol n-propyl ether.

In one embodiment of the invention, the silanol containing molecule comprises triethylsilanol. Triethylsilanol is preferably disposed in an aqueous solution including propylene glycol n-propyl ether. The contacting step can comprise flowing a carrier gas through a solution comprising the silanol end group containing molecule to form an aerosol, and directing the aerosol towards the surface to be treated.

The silanol containing molecule can be a fragrant silanol. In this embodiment, the fragrant silanol is selected from $Ar(CH_2)_aR_1R_2SiOH$, where Ar is any phenyl or substituted phenyl group such that the substitution has a molecular weight of <60, a is <5, and $R_1$ and $R_2$ are Ar or alkyl or fluoro alkyl group with less than 4 carbons. The fragrant silanol can be phenethyldimethylsilanol or benzyldimethylsilanol.

In an alternate embodiment, the silanol is blended with a hydroxy containing material, such as a hydroxy containing polymer. The hydroxy containing polymer can comprises a siloxane, such as polydimethylsiloxane (PDMS).

A composition of matter comprises a low molecular weight silanol end group containing molecule blended with a polymer or non-polymeric hydroxy containing material, or dissolved in aqueous solution along with an ether-based cosolvent. The low molecular weight silanol end group containing molecule is a specie selected from silanols ($R_1R_2R_3SiOH$), siloxanediols $HO(R_1R_2SiO)nH$ or siloxanols $HO(R_1R_2SiO)nSiR_1R_2R_3$, where $R_1$, $R_2$ and $R_3$ are selected from 1 to 4 carbon alkyl or fluoroalkyl moieties, or vinyl, or aryl groups and n is <6. The silanol silanol can comprise triethylsilanol, diphenylmethylsilanol, t-butyldimethylsilanol, n-butyldimethylsilanol, n-propyldimethylsilanol, ethyldimethylsilanol, vinylphenylmethylsilanol, phenyldimethylsilanol, 3,3,3-trifluoro propyldimethylsilanol, benzyldimethylsilanol or phenethyldimethylsilanol, or mixtures thereof. When combined with a polymer, the polymer is preferably a hydroxy containing polymer, such as a siloxane.

BRiEF DESCRIPTION OF THE DRAWINGS

A fuller understanding of the present invention and the features and benefits thereof will be obtained upon review of the following detailed description together with the accompanying drawings, in which.

DETAILED DESCRIPTION

Figure 1:
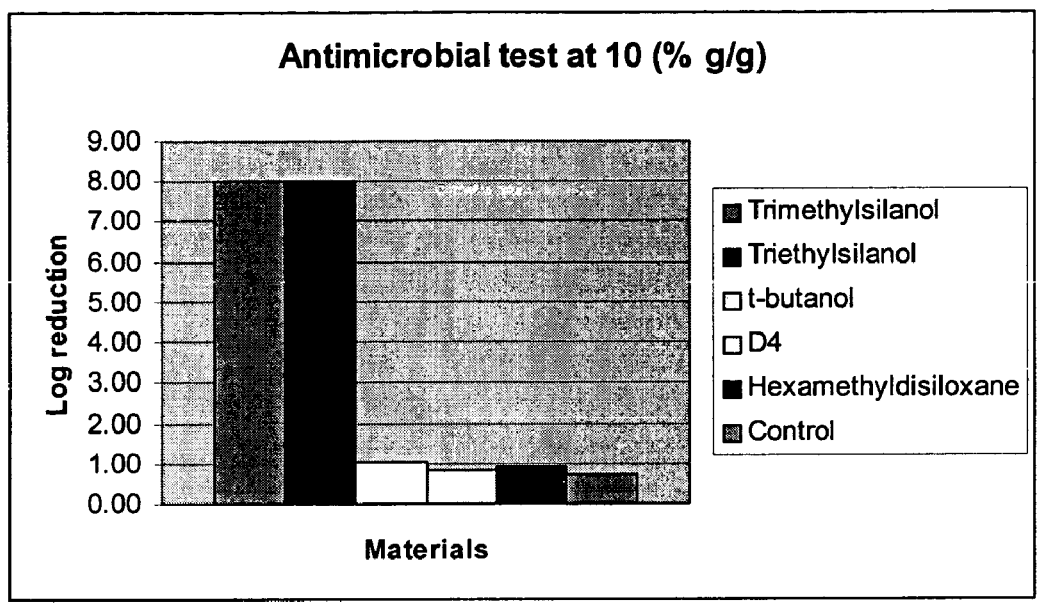
FIG. 1 shows results from an antimicrobial test run at 10 (% g/g) using some biocides according to the invention (trimethylsilanol and triethylsilanol), as compared to other materials.

It has been found that low molecular weight silanol (SiOH) terminated species are effective as transitory biocides. It is believed that silanol groups act as biocides for a short period of time and then either break down in their environment to form $CO_2$, $H_2O$ and $SiO_2$, or rapidly condense into siloxanes with the elimination of water. As a result of their transitory nature and the products formed, biocides according to the invention are highly environmentally inert. As defined herein, the term "biocide" refers to a chemical agent that is capable of destroying living organisms. For example, low molecular weight silanol end group containing molecules according to the invention have been shown to be effective biocides against *E. coli* and an anthrax surrogate, *bacillus cereus* spores. *Bacillus cereus* is very similar to the *bacillus anthracis*, which is known to cause anthrax.

A method of destroying living microorganisms includes the steps of contacting at least one target microorganism with low molecular weight silanol end group containing molecules. The low molecular weight silanol end group containing molecules are selected from silanols ($R_1R_2R_3SiOH$), siloxanediols $HO(R_1R_2SiO)nH$ or siloxanols $HO(R_1R_2SiO)nSiR_1R_2R_3$, where $R_1$, $R_2$ and $R_3$ are selected from 1 to 4 carbon alkyl or fluoroalkyl moieties, or vinyl, or aryl groups and n is <6. It may be possible for R to also include H. However, the Si—H bond is relatively unstable towards hydrolysis leading to formation of SiOH.

In a related embodiment of the invention, the biocidal low molecular weight silanol containing moiety is fragrant. The fragrant silanol can be selected from $Ar(CH_2)_aR_1R_2SiOH$, where Ar is any phenyl or substituted phenyl group such that the substitution has a molecular weight of <60, where a is <5, and $R_1$ and $R_2$ are Ar or alkyl or fluoro alkyl group with less than 4 carbons. For example, the fragrant silanol can be phenethyldimethylsilanol, or benzyldimethylsilanol.

Silanol terminated low molecular silicones are environmentally benign because of their transitory nature and rapid formation into environmentally inert products. Moreover, such materials are inexpensive since silanols are an integral part of the already mature silicone industry.

The low molecular weight silanol (SiOH) terminated species are generally provided in a solvent, such as water. However, as described below, a suitable cosolvent can improve the effectiveness of the invention. In a preferred embodiment, the silanol end group containing molecules are silanols ($R_1R_2R_3SiOH$), and the silanols are used together in a system with water as a solvent and an ether-based cosolvent. The cosolvent is preferably propylene glycol ether, most preferably propylene glycol n-propyl ether (PnP). Propylene glycol n-propyl ether has been found to significantly improve the solubility and antimicrobial effect of certain silanols in aqueous solution.

Ethers such as propylene glycol n-propyl ether and related materials have an excellent balance of hyprophobic and hydrophilic properties. As demonstrated in the Examples, the antimicrobial effect of diphenylmethylsilanol, t-butyldimethylsilanol, and triethylsilanol was found to be significantly enhanced with the cosolvent propylene glycol n-propyl ether, whereas non-silanols tested did not enhance antimicrobial performance with the addition of propylene glycol n-propyl ether. The result obtained suggests a possible catalytic effect by the cosolvent when it is mixed with silanols.

Silanols are generally prepared from low cost processes, such as the hydrolysis of chlorosilanes. Methylchlorosilanes are manufactured in quantities of more than a billion pounds per year. Though the exact half-life of the silanols is not exactly known, these materials are known to readily convert to $CO_2$, $H_2O$ and $SiO_2$ in the environment making them environmentally friendly agents. Silanols are generally easily soluble in organic solvents and water and can be utilized as solutions or neat. Some of the silanols have limited shelf life and may require cold storage.

In one embodiment, the transitory biocide is based on substituted silanes. Silanes are the basic building blocks of silicon chemistry. A silane is a monomeric silicon containing molecule with a chemical formula in which four substituent groups are attached to the silicon atom. The R groups can be the same or different. They can be nonreactive or reactive, with the reactivity being inorganic or organic. Special characteristics can be added to the silicon molecule by adding R groups comprising nonreactive groups, such as methyl, the higher alkyls generally up to 4 carbons, and vinyls. Aryls including phenyl may also be effective R groups.

The R group can be selected to achieve desired properties of the silane. For example, when R is methyl, hydrophobicity and low surface tension generally result. Higher alkyls generally provide organic-compatibility. Aryls such as phenyl generally provide thermal stability, organic-compatibility and hydrophobicity. In most applications for the invention, significant water solubility and volatility is preferred. Preferred silanol species according to the invention include triethylsilanol and silanols containing longer alkyl chains.

As noted above, the low molecular weight silanol end group containing molecules can be silanols ($R_1R_2R_3SiOH$), siloxanediols $HO(R_1R_2SiO)nH$ or siloxanols $HO(R_1R_2SiO)nSiR_1R_2R_3$, where $R_1$, $R_2$ and $R_3$ are selected from 1 to 4 carbon alkyl or fluoroalkyl moieties, or vinyl, or aryl groups and n is <6. In a preferred embodiment, n is 4 or less. As with the substituted silanes, R can be the same or different. They can be nonreactive or reactive, with the reactivity being inorganic or organic. Special characteristics can be added to the silicon molecule by adding R groups comprising nonreactive groups, such as methyl, the higher alkyls, vinyls, and aryls including phenyl. Preferred siloxane species include trisiloxanediol, disiloxanediol.

As noted above certain silanols according to the invention are fragrant. The fragrant silanol are selected from $Ar(CH_2)_a R_1R_2SiOH$, where Ar is any phenyl or substituted phenyl group such that the substitution has a molecular weight of <60, where a is <5, and $R_1$ and $R_2$ are Ar or alkyl or fluoro alkyl group with less than 4 carbons, such as phenethyldimethylsilanol and benzyldimethylsilanol. The minimum lethal concentration of silanols was found to be lower than the corresponding alcohols suggesting that the antimicrobial effect of silanols is better than their corresponding alcohols. (See Example II).

There are several methods of forming siloxanes including step-growth polymerization (a type of polycondensation) and ring-opening copolymerization. Step-growth polymerization of linear polysiloxanes include either homocondensations of silanol-terminated siloxanes or heterocondensations of silanol-terminated species with monomers containing good leaving groups. Both of these reactions are respectable ways of forming polysiloxanes, however homocondensation is more commonly used. Homocondensation, also called polycondensation, is a reaction in which two molecules including the silanol group condense to form a polymer. This is illustrated in the reactions below (more accurately indicated as equilibrium reactions where the equilibria lie strongly to the right direction):

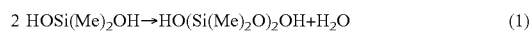
$$2\ HOSi(Me)_2OH \rightarrow HO(Si(Me)_2O)_2OH + H_2O \quad (1)$$

$$2\ HO(Si(Me)_2O)_2OH \rightarrow HO(Si(Me)_2O)_4OH + H_2O \quad (2)$$

Low molecular weight silanol end group containing molecules can also be obtained from larger molecules, including polymers such as PDMS through hydrolysis. In addition, carbinol groups, COH, are found in many natural and synthetic polymers. COH functionality can be easily converted to $COSiR_3$ functionality which can be used to slow or control release of silanols through hydrolysis. Thus, treatment of a variety of substrates, such as fabrics, should be possible. The full extent of the potential biocide activity has not yet been established. However, it is assumed that silanols according to the invention might be a useful antimicrobial for a wide range of microorganisms, such as those responsible for Legionaire's Disease.

There are a variety of methods of dispensing the silanols according to the invention that can be used to obtain the desired antimicrobial effect. Silanols according to the invention can be used neat or in solutions of water or organic solvents. Once in solution or in liquid form, these materials can be atomized using a carrier gas, such as to treat a contaminated room or a room suspected of being contaminated.

In another embodiment of the invention, vapor from silanol end group containing molecules is applied to a region to be treated without the need for a solvent. For example, a carrier gas (e.g. air or $N_2$) can be passed over a sample of solid or liquid silanol according to the invention to form an aerosol, such as triethylsilanol (a solid at STP) which carries vapor phase triethylsilanol to a desired location. The silanol end group sample can be heated to increase the partial pressure of the silanol end group containing vapor.

In another embodiment, materials according to the invention can be to used as additives in solid materials. Si—O—C bonds can be formed which upon hydrolysis release silanols. Thus, this chemistry allows for binding the silanols to a variety of hydroxyl containing materials, such as fabrics or metal oxide surfaces. This chemistry can be used both for surfaces or in the case of polymers for intra molecular bound carbinol.

When covalently bound to or intermixed with substrate materials, materials according to the invention can provide controlled release rates. The solid materials are preferably hydroxy containing materials, such as hydroxy containing polymers, and non-polymeric hydroxides, such as metal hydroxides. Hydroxy containing polymers include silicones, such as PDMS. Although generally not preferred, nonhydroxy containing polymers may also be used. Materials according to the invention can also be bound to fillers, such as in polymer composites. For example, the polymer composite can be a silicone elastomer, such as a PDMS elastomer.

As noted above, biocides according to the invention can be generated through hydrolysis of compositions which include ~~~SiOC~~~ bonds, and likely ~~~SiOSi~~~ bonds. Many natural and synthetic polymers contain ~~~COH functionalities such as wood, paper and cotton. These groups can be easily converted to ~~~COSi(CH$_3$)$_3$ by reaction with silylating agents such as (CH$_3$)$_3$SiNHSi(CH$_3$)$_3$. Once formed, ~~~COSi(CH$_3$)$_3$ containing molecules release (CH$_3$)$_3$SiOH via hydrolysis.

One class of silicon containing compounds which are easy to obtain are the silicon alcoxides which can be view as the condensation product of a carbinol and silanol to form the Si—O—C moiety. These moieties are in equilibrium with water or water vapor to form the original carbinol and silanol. Thus, silanols can be covalently bound to hydroxyl containing molecules or substrates such as fabric or carbinol containing polymers usually with silazane precursors and then slowly released through hydrolysis of water from the environment. The binding of the silanols moiety is the common silylation reaction used in retro synthetic strategies of drug molecules and is currently used in many new separation strategies. In summary, tri or di-organo silanols are generally more acidic, more hydrophobic, have the possibility of extra coordination with biocatalyst structures and can be chemically bound through the hydrolysable Si—O—C bond such as those found in many fabrics or to metal oxide surfaces containing the M-OH functionality.

In one exemplary embodiment, silanols can be formulated into urethanes by processes described below and cured. Core(silica)/shell nano particles of the silanols can also be prepared as desribed below and formulated into the urethane top coats and also into abrasion resistant coatings (ARCs).

Formulating Silanols Into Urethane Top Coat

Silanols can be mixed with a colloid mill or other similar high sheer mixer into the highest viscosity of the resin. The resin can then be cured in the normal manor. The cured specimens are preferably examined microscopically and by SEM to determine if there is any significant phase separation. The method is adjusted to avoid separation if present. Another method adds silanols as silazane precursors which can chemically react with excess COH functionality to form hydrolysable C—O—Si bonds.

Preparing Silica Core/Shell Nano Particles Containing Silanols

Core-shell silica nano-particles can be synthesized and filled with selected silanols. Particles can be synthesized similar to a technique reported in the literature by Underhill et al. [R. S. Underhill, A. V. Jovanovic, S. R. Carino, M. Varshney, D. O. Shah, D. M. Dennis, T. E. Morey, and R. S. Duran, Oil-filled silica nanocapsules for lipophilic drug uptake: Implications for drug detoxification therapy, Chemistry of Materials 14 (2002) 4919-4925] In effect, an oil or hydrophobic micelle is formed in a solution and then coated with a silica shell. The initial micelle serves as the core of the core-shell particle system A solution of water, an oil, and a surfactant can be used to form a micro emulsion. The ratio of the surfactant to oil can be used to control the size of the core of the particle. Materials used in this step are usually a saturated oil such as hexadecane and readily available surfactants such as BRIJ-97™.

To this solution a surfactant-like silane is preferably added, such as octadecyltrimethoxysilane (OTMS). OTMS has a long hydrophobic carbon chain which will point into the micelles formed in the first step. The OTMS will in effect coat the surface of the micelle and can be readily hydrolyzed to promote condensation. At this stage the shell is very thin and weak.

The next step involves the growth of the actually shell around the micelle core. Tetramethoxysilane (TMOS) can be employed to increase the thickness. Small amounts of TMOS can be added to the OTMS-Micelle solution and stirred for a variable amount of time. The reaction is preferably done in neutral conditions to reduce condensation of TMOS in the free solution. The TMOS will deposit a silica shell on the outside of the particle with thickness controlled by reaction time and TMOS concentration The resulting particles can be characterized by particle size measurements using light scattering techniques or by staining the core of the particle with $OsO_4$, a known technique. The core/shell particles should function like normal silica particles with similar sizes. They can be mixed into one component of the urethane resin with the aid of a three role mill and the cure and evaluated as described above.

Preparation of Clear Core/Shell ARC Coatings

It is known how to formulate optically clear abrasion resistant coatings (ARC's). These materials can be prepared by hydrolysis of methyltrimethoxysilane with acid stable colloidal silica at a pH~4.5 followed by stabilization of the solution with EPA and butanol. The systems are preferably cured with organotin catalysts. It is should be a simple matter to incorporate a small portion of the pseudo silica core/shell particles containing silanols.

This largely non-volatile embodiment of the invention provides several advantages over conventional biocides used for anti-fouling. As noted in the background, conventional antifouling agents are plagued by residual long term toxicity and lack of effectiveness against a broad class of microorganisms. In contrast, materials according to the invention including silanol terminated low molecular weight silicones and substituted silanes are environmentally benign because of their transitory nature. Non-volatile embodiments of the invention are shown to be effective marine antifouling agents in Example II below.

Regarding the volatile inventive embodiment, as shown in the Example I below, materials according to the invention demonstrate a high level of effectiveness as antimicrobial materials for *E. coli*. These materials are also expected to be effective against anthrax spores since the marine organisms studied were also spore based organisms, as well as a variety of other microbials, and likely molds as well.

The invention is expected to have a wide range of commercial and military applications. Commercial applications include fumigation and a wide variety of surface treatments. The fragrant silanols are particularly well suited for use as fabric treatment (e.g. softener), as well as antimicrobial fragrances. For example, phenethyldimethylsilanol which as noted above provide a floral smell, can be used as a hard surface cleaner for the interior of motor vehicles, bathrooms including toilets, bathtub, kitchen appliances, floor cleaners. Benefits to the military include a low cost technology, environmentally friendly material, facile application techniques, and high probability of efficacy against a broad range of potential bioterrorist events.

EXAMPLES

It should be understood that the Examples described below are provided for illustrative purposes only and do not in any way define the scope of the invention.

Example I

Bioactivity Tests

Bioactivity (toxicity) tests were performed using silanols according to the invention along with some controls. *E. coli* was provided as the target microorganism. The Plate counts and dilution method as described in American Health Association (APHA), American Water Works Association, and Water Environment Federation 1998 standard Methods for the Examination of Water and Wastewater. $20^{th}$ ed. L. S. Clesceri, A. E. Greenberg, A. D. Eaton (eds.) Washington, D.C. was employed to measure the number of viable cells after the bioactivity tests. The collected sample underwent serial dilutions in which the original sample collected was diluted in a series of dilution tubes. Each succeeding dilution tube will have only one-tenth the number of microbial cells as the preceding tube. Then the samples of the dilution were used to inoculate Petri plates containing solid medium. The sample on the plates was plated evenly over the surface of the solid medium. Colonies grew only on surface of medium and could be counted. This count was used to estimate the number of viable bacterial in the original sample.

FIG. 1 shows results from an antimicrobial test at 10 (% g/g) concentration using some molecules according to the invention as compared to other materials against *E. coli*. Log reduction represents the number of *E. coli* eliminated through the silanol or other chemical treatment. The experiments were operated for an hour with proper stirring in aqueous solution. The chemicals tested included silanols, trimethylsilanol and triethylsilanol, t-butanol, $D_4$(octamethylcyclotetrasiloxane) and hexamethyldisiloxane. Trimethylsilanol and triethylsilanol exhibited a high antimicrobial effect as compared to t-butanol, $D_4$, hexamethyldisiloxane and the water only control. Log reduction 8 represents the detection limit for the experiment performed, and thus represents complete removal.

Figure 2:
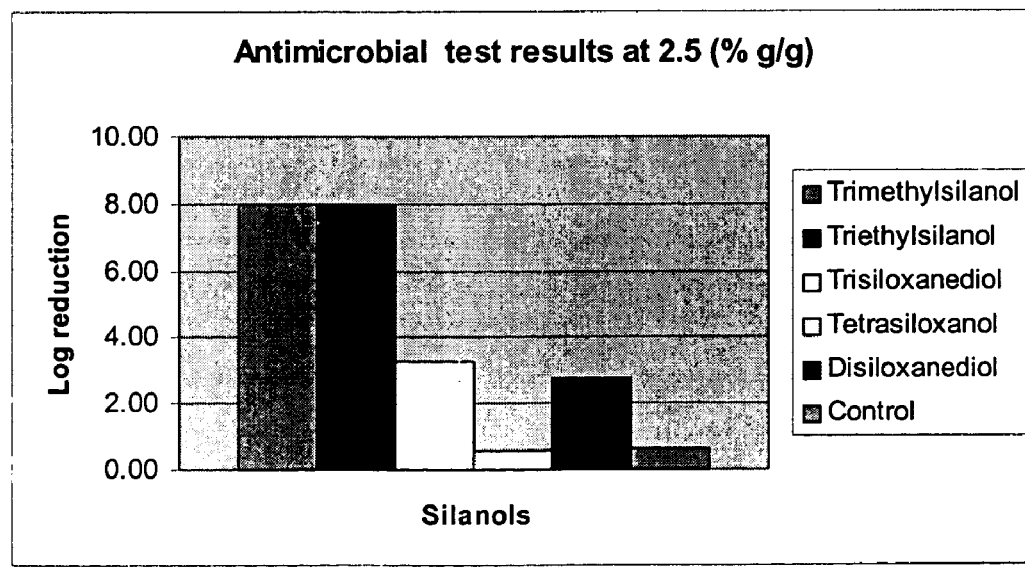
FIG. 2 shows results from an antimicrobial test run at a lower concentration 2.5 (% g/g) as compared to the concentration used to obtain the data shown in FIG. 1. Even at the 2.5 (% g/g) concentration, trimethylsilanol and triethylsilanol tested demonstrated a strong antimicrobial effect, once again providing a 8 log reduction detection limit.

FIG. 2 shows antimicrobial test at a lower (2.5% g/g) concentration using the silanols, trimethylsilanol and triethylsilanol, as well as trisiloxanediol, tetrasiloxanol, disiloxanediol and the water control. Even at the 2.5 (% g/g) concentration, silanols tested demonstrated a strong antimicrobial effect, once again at the log reduction 8 detection limit.

Figure 3:
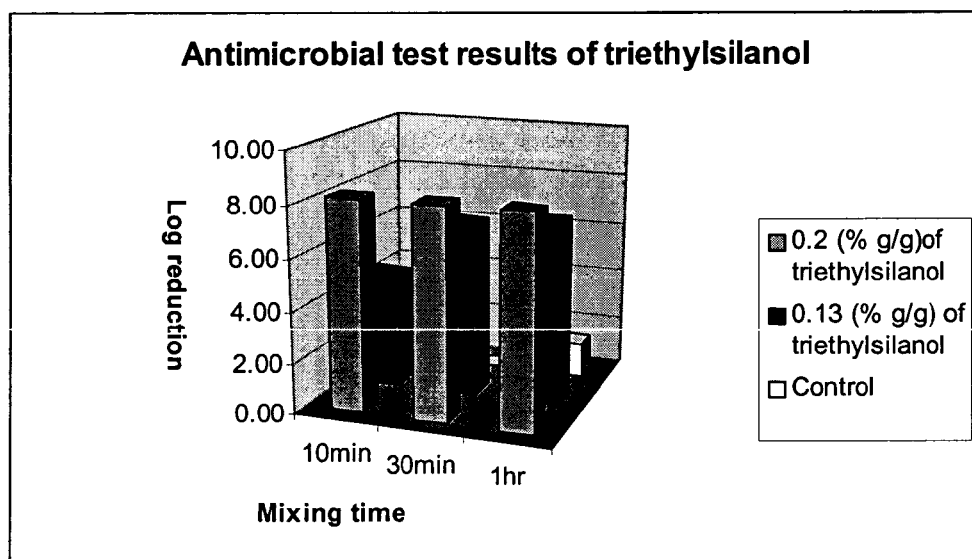
FIG. 3 shows results from antimicrobial tests with triethylsilanol at even lower concentrations (<0.2 (% g/g) and 0.13 (% g/g) as compared to the data shown in FIGS. 1 and 2. Triethylsilanol showed a strong effect reducing *E. coli* of more than eight orders of magnitude to below the detection limit at the low concentration, 0.2 (% g/g), and in only a 10 minute mixing.

FIG. 3 shows antimicrobial tests with triethylsilanol at even lower concentrations as compared to the data shown in FIGS. 1 and 2. Triethylsilanol showed a strong effect reducing *E. coli* more than eight orders of magnitude to below detection limits at the 0.2 (% g/g) concentration in only a 10 minute mixing.

The substituent effect was also investigated. Silanols containing different substituent R groups were tested to determine the substituent effect against *E. coli*. It is known that the hydrophobicity and acidity of silanols vary with the particular R-group substituents. The different degree of hydrophobicity and acidity of silanols may induce a different degree of toxicity of silanols against the microbials. Greater hydrophobicity and acidity may lead to the better antimicrobial effect due to the favored interactions. Silanol samples were prepared through the hydrolysis of chlorosilanes and again tested against *E. coli*.

Figure 4:
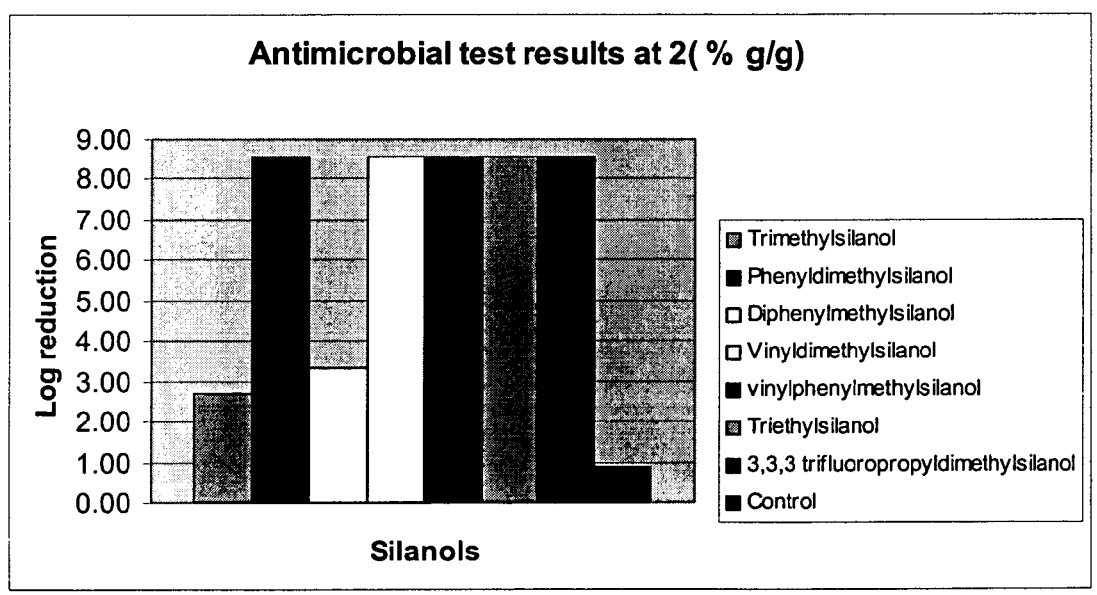
FIG. 4 shows results from an antimicrobial test run with silanols at 2 (% g/g) concentration for various R-group substituted silanols according to the invention. The results show more than eight log reduction indicating a complete removal of *E. coli*.

FIG. 4 shows antimicrobial test result with silanols at 2 (% g/g) for various R-group substituted silanols according to the invention. The results show more than eight log reduction indicating a complete removal of *E. coli* from the test because the initial concentration of *E. coli* is no greater than $10^8$ cfu/ml (Colony forming unit). Phenyldimethylsilanol, vinyldimethylsilanol, vinylphenylmethylsilanol, triethylsilanol and 3,3,3-trifluoropropyldimethylsilanol all provided eight log reductions.

Figure 5:
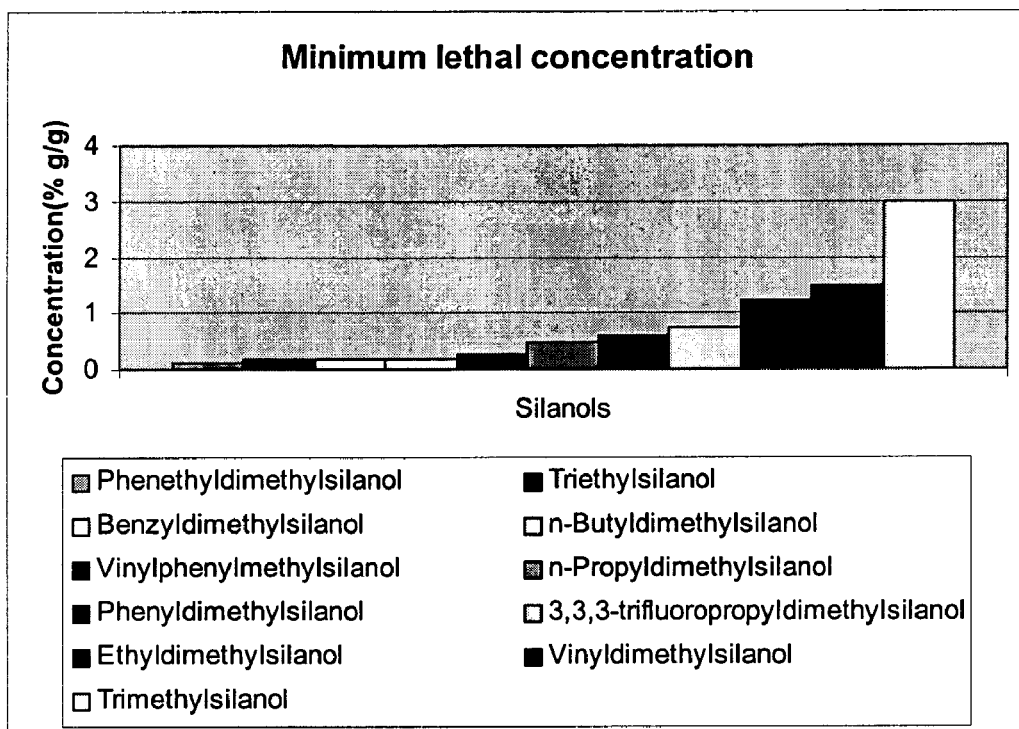
FIG. 5 shows the minimum lethal concentration measured for various R-group substituted silanols according to the invention against *E. coli*.

FIG. 5 shows the minimum lethal concentration measured for various silanols according to the invention against *E. coli*. The minimum lethal concentration against *E. coli* for each silanol is defined as the maximum dilution of the product that will kill a test organism. The substituent R groups, phenyl and vinyl, were found to improve the bioactivity of silanols compared to trimethylsilanol which has methyl groups. Triethylsilanol showed a strong antimicrobial effect as shown FIG. 5. The antimicrobial effect increased with an increase in the number of the alkyl chain of the substituent R, in the order of methyl<ethyl<n-propyl<n-butyl as shown FIG. 5.

Figure 6:
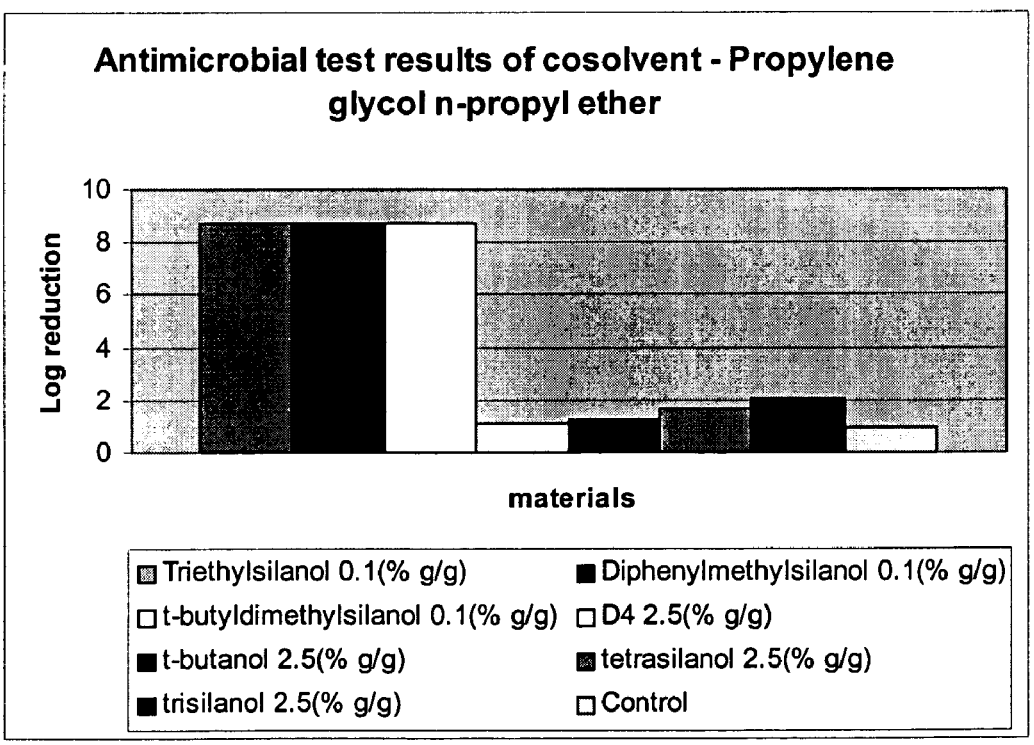
FIG. 6 shows results from antimicrobial test results using the cosolvent propylene glycol n-propyl ether together with molecules including silanols according to the invention. The antimicrobial effect of diphenylmethylsilanol, t-butyldimethylsilanol, and triethylsilanol are shown providing a 8 log reduction at 0.1% g/g with the cosolvent propylene glycol n-propyl ether, whereas $D_4$ $((CH_3)_2SiO)_4$ and t-butanol did not provide significant bioactivity even with the cosolvent.

As noted above, addition of certain cosolvents can improve results obtained, termed herein as the "cosolvent effect". Experiments were performed using the cosolvent propylene glycol n-propyl ether, which was found to improve the solubility and antimicrobial effect of silanols in aqueous solution. As shown in FIG. 6, the antimicrobial effect of diphenylmethylsilanol, t-butyldimethylsilanol, and triethylsilanol provide 8 log reduction at 0.1% g/g) with the cosolvent propylene glycol n-propyl ether, whereas $D_4$ $((CH_3)_2SiO)_4$ and t-butanol did not provide significant bioactivity even with the cosolvent.

Figure 7:
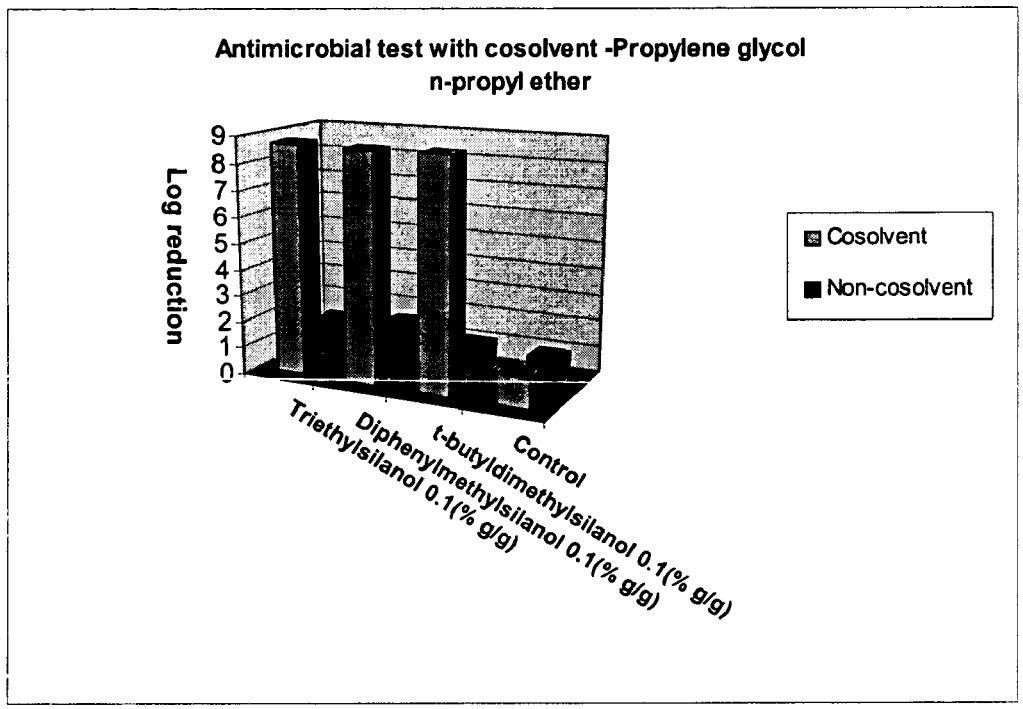
FIG. 7 shows the cosolvent enhancement on antimicrobial effect for diphenylmethylsilanol, t-butyldimethylsilanol and triethylsilanol as compared to a non-cosolvent control.

FIG. 7 shows results from antimicrobial test results using the cosolvent propylene glycol n-propyl ether together with chemicals including silanols according to the invention (shown in FIG. 6), as compared to no cosolvent controls. Although log reduction 8 was achieved at a concentration of 0.1 (% g/g) for silanols according to the invention including trimethyisilanol, diphenyimethylsilanol, and t-butyldimethylsilanol, the reduction without the cosolvent for the same chemicals was only 1 to 2 log.

Figure 8:
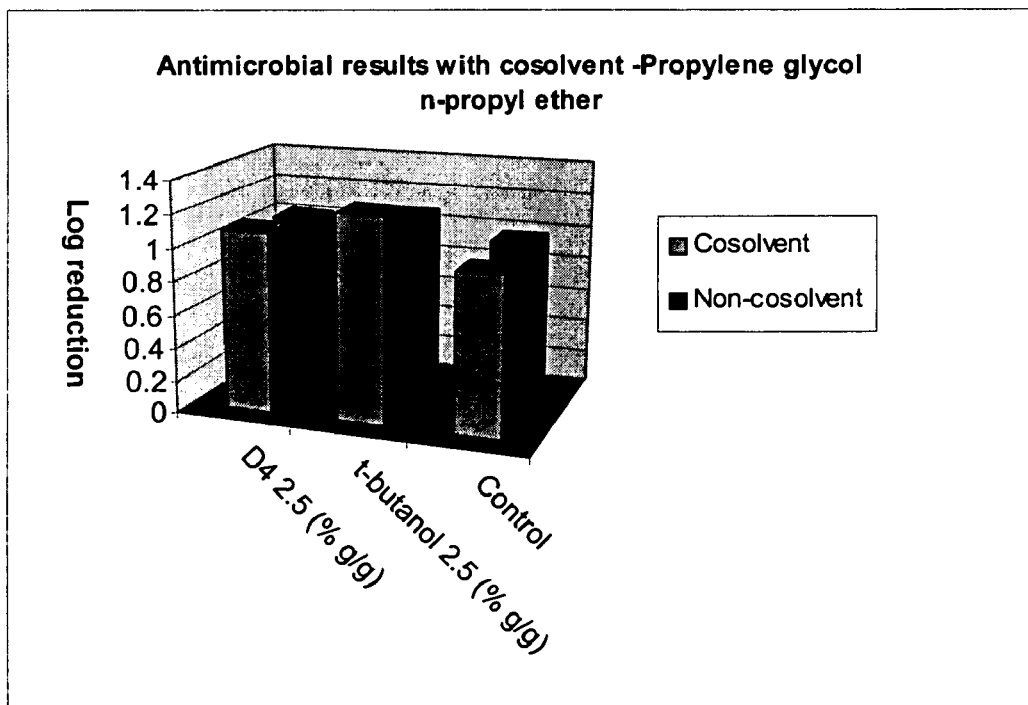
FIG. 8 shows antimicrobial test results for $D_4$ (octamethylcyclotetrasiloxane)and t-butanol at a 2.5% g/g concentration with cosolvent and no-cosolvent. The antimicrobial effect was not measurably improved by addition of cosolvent as compared to data from the silanols according to the invention shown FIG. 7.

FIG. 8 shows antimicrobial test results for $D_4$, $((CH_3)_2 SiO)_4$ and t-butanol (2.5% g/g) with the cosolvent and without cosolvent. The bioactivity was only 1 to 2 log both with and without the cosolvent propylene glycol n-propyl ether.

Figure 9:
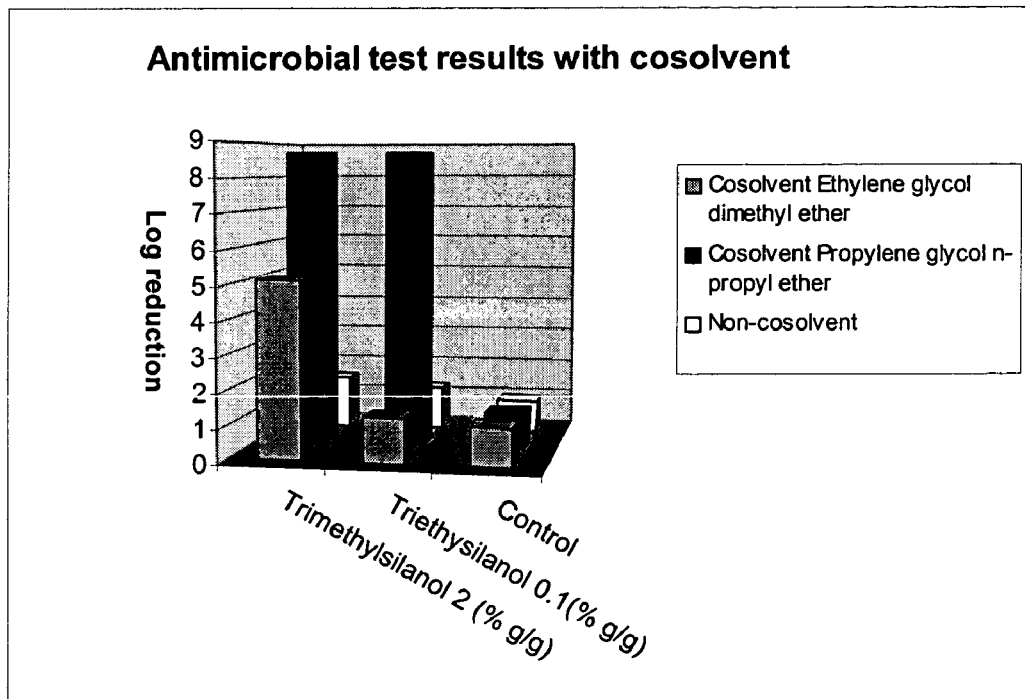
FIG. 9 shows antimicrobial test results showing results from silanols with different cosolvents and no cosolvent. Propylene glycol n-propyl ether was found to be more effective for enhancement of antimicrobial effect of silanols according to the invention compared to ethylene glycol dimethyl ether, or no cosolvent.

FIG. 9 shows antimicrobial test results of silanols with a different cosolvent and no cosolvent. Propylene glycol n-propyl ether was found to be more effective for enhancement of antimicrobial effect of silanols according to the invention compared to ethylene glycol dimethyl ether, or no cosolvent.

Example II

Fragrant Silanol Containing Moieties

Dimethyl benzyl carbinol (2-methyl-1-phenyl-2-propanol) is known fragrant ingredient. It releases floral, rose, green, and an oily odor. The corresponding silanols have also found to provide similar fragrance properties, and also function as a biocides. As noted above, the fragrant biocidal low molecular weight silanol can be selected from $Ar(CH_2)_a R_1R_2SiOH$, where Ar is any phenyl or substituted phenyl group such that the substitution has a molecular weight of <60, where a is <5, and $R_1$ and $R_2$ are Ar or alkyl or fluoro alkyl group with less than 4 carbons.

Antimicrobial test was carried out to compare the bioactivity of fragrance ingredient of alcohols and the corresponding silanols according to the invention against *E. coli*. Alcohols, 2-methyl-1-phenyl-2-propanol corresponding to benzyldimethylsilanol, 2-methyl-4-phenyl-2-butanol corresponding to phenethyldimethylsilanol, were obtained from Sigma-Aldrich, and the silanols were prepared by the hydrolysis of chlorosilane.

Nine (9) ml of D.I. water was mixed with 1 ml of *E. coli* solution, and antimicrobial materials for 1 hr with magnetic stirring, then sampling was carried out. The plate counting method as described above was employed to measure the viability of the *E. coli*. Results are shown in Table 1 below.

TABLE 1

Minimum Lethal Concentrations (MLC) of tested materials

| Materials | Range of Minimum lethal concentration (% g/g) |
|---|---|
| 2-methyl-1-phenyl-2-propanol (Aldrich) | 1–0.65 |
| 2-Methyl-4-phenyl-2-butanol (Aldrich) | 0.5–0.25 |
| Phenethyldimethylsilanol (UF) | 0.1–0.075 |
| Benzyldimethylsilanol (UF) | 0.5–0.2 |

Figure 10:
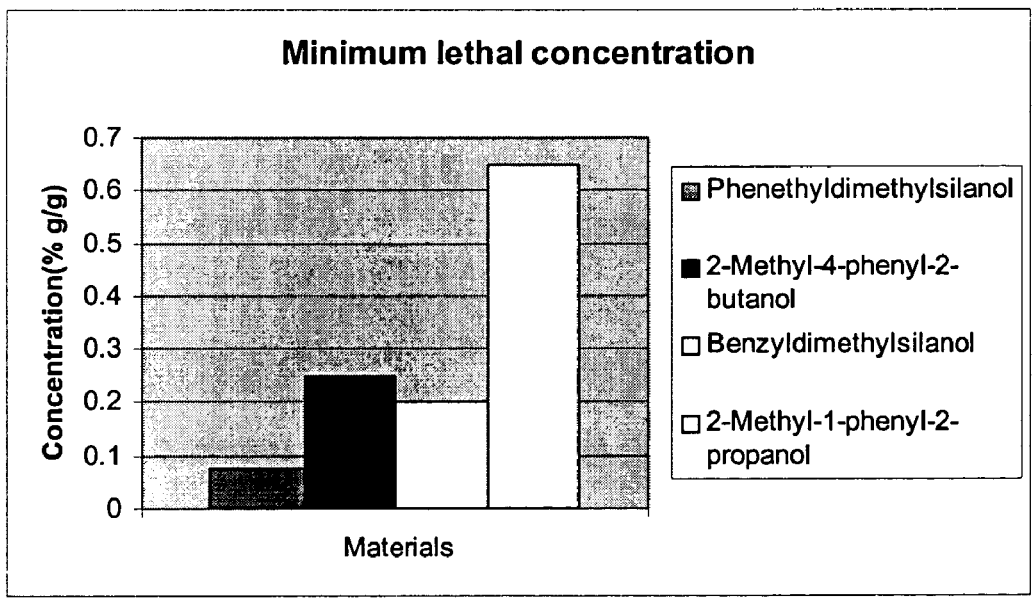
FIG. 10 shows the minimum lethal concentration measured for various fragrant silanols according to the invention as compared to their corresponding alcohols against *E. coli*.
Figure 11:
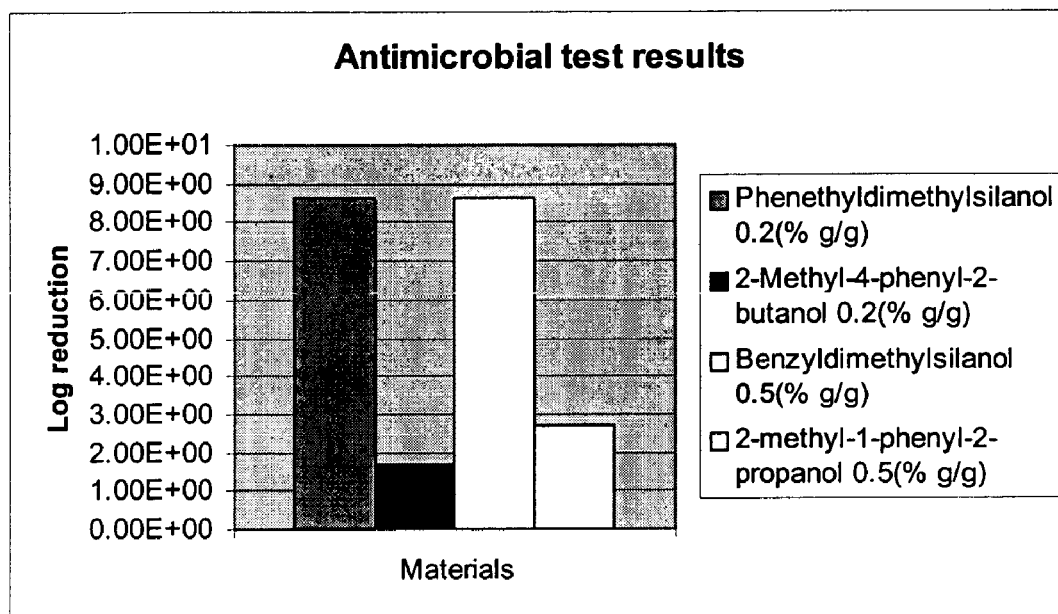
FIG. 11 shows results from an antimicrobial test run with fragrant silanols according to the invention as compared to their corresponding alcohols against *E. coli*. The fragrant silanols are seen to provide more than eight log reduction indicating a complete removal of *E. coli*.

FIG. 10 shows the minimum lethal concentration measured for various fragrant silanols according to the invention as compared to their corresponding alcohols against *E. coli*. The minimum lethal concentration of the silanols phenethyldimethylsilanol and Benzyldimethylsilanol were found to be lower than their corresponding alcohols demonstrating that the silanols are more effective biocides. FIG. 11 shows results from an antimicrobial test run with fragrant silanols according to the invention as compared to their corresponding alcohols against *E. coli*. The fragrant silanols are seen to provide more than eight log reduction indicating a complete removal of *E. coli*. The odor of the prepared silanols were found to be similar to the corresponding alcohols.

Example III

Anti-Fouling Efficacy

In this Example, the effect on anti-fouling efficacy by incorporating silanols according to the invention into the siloxane containing polymer PDMS was tested. PDMS is a colorless, transparent polymer. The PDMS used in this Example was Silastic T2 base (a PDMS elastomer available from Dow Corning) which comprises a PDMS elastomeric composite. The PDMS sample was evaluated with respect to Ulva (green algae spores). Silicones are known to exhibit excellent marine fouling release properties compared to other materials because of low surface energy, low modulus, high flexibility and low glass transition temperature. However, the generation rate of silanols from unmodified PDMS surfaces is low, which limits its potential effectiveness. Thus, in the Example described below low molecular weight end terminated silanols according to the invention were incorporated into PDMS as described above to form composites in an attempt to enhance the marine fouling release properties on the silicone surface.

Slide Preparation

All slides are prepared with the following mixing ratio and the curing conditions: Mixing Ratio:T2:Curing agent:Silanol terminated samples=10:1:2%/total (by wt) Curing condition: 50° C./5 hr Test condition for each slide type: 3—*Ulva* (syn. enteromorpha)→ Settlement 3—*Ulva* (syn. enteromorpha)→ Release A reference sample, mixed with the Silastic T2 base and curing agent only, was prepared as well. Six replicates of each type were made. Film thicknesses ranged from 930 μm to 1040 μm.

| No. | Chemical structure | Chemical name | No. of slide | Source |
|---|---|---|---|---|
| 1 | CH₃—Si(CH₃)(CH₃)—OH | Trimethylsilanol M.W (g/mol): 90 | 6 | Lab |
| 2 | CH₃—Si(CH₃)(CH₃)—O—Si(CH₃)(OH)—O—Si(CH₃)(CH₃)—CH₃ | Trisiloxanol (Hepta methyl 3-trisiloxanol) M.W (g/mol): 238 | 6 | Clariant |

-continued

| No. | Chemical structure | Chemical name | No. of slide | Source |
|---|---|---|---|---|
| 3 | (structure shown) | Tetrasiloxanol (Tris(trimethylsiloxy)silanol) M.W (g/mol): 312 | 6 | Clariant |
| 4 | Reference sample | Described above | 6 | Dow Corning |

MilliQ water was added to tubes immediately. Before the start of the experiment, all samples were transferred to individual compartments of quadriperm dishes which were filled immediately with artificial seawater (ASW). The samples were left in ASW for 1 h before the experiment was started.

The ASW was drained from the dishes and 10 ml of spore suspension ($1.5 \times 10^6$ ml$^{-1}$) added and the dishes were placed in darkness for 1 h. After the 1 h incubation, the spore liquid was poured into glass vials which were placed in the light. Swimming spores move away from the light so this test checks that the spores are viable at the end of the 1 h assay period.

The slides were rinsed in ASW to remove unsettled spores. Three replicates were fixed in 2.5% glutaraldehyde to provide settlement data and three replicates were run in the flow channel at 55 Pa wall shear stress before fixation. Percentage removal was calculated from spore counts from the before and after flow treatments.

Results

Viability Tests

Spores moved away from the light and collected on the sides and bottom of the tubes. However, the rate of movement away from the light was slower for spore liquid removed from samples 2 and 3 (trisiloxanol and tetrasiloxanol comprising polymers, respectively). Inspection the following day showed bleaching of the settled spores in samples 2 & 3 and some possible loss of green color from sample 1 (trimethylsilanol comprising polymer).

Spore Adhesion Assay

The spore settlement and removal data are only presented for the reference PDMS (sample 4) and sample 1 (trimethylsilanol comprising polymer). Many of the spores settled on samples 2 and 3 showed poor autofluorescence indicating loss of chlorophyll and inspection in transmitted light revealed a high proportion of misshapen spores, some with outstretched flagella indicating they had lost motility and not undergone normal settlement to the surface. There was also cell debris distributed across the surface. The spores on sample 1 appeared to settle normally although some were not as brightly autofluorescent as on the standard PDMS, suggesting some added toxicity associated with its surface.

Trimethylsilanol was intentionally added to PDMS to understand the possible chemical effect of a hydrolyzed PDMS surface. When PDMS is hydrolyzed, trimethylsilanol is generated. The chemical effect hypothesized was the toxicity of the silanol species, for example trimethylsilanol, reducing spore settlement in the first place. Spore counts were collected from both the reference PDMS sample (sample 4) and the trimethylsilanol comprising PDMS sample (sample 1), before (denoted as −flow) and after the replicates were exposed to hydrostatic pressure comprising a 55 Pa wall shear stress (denoted as +flow).

Figure 12:
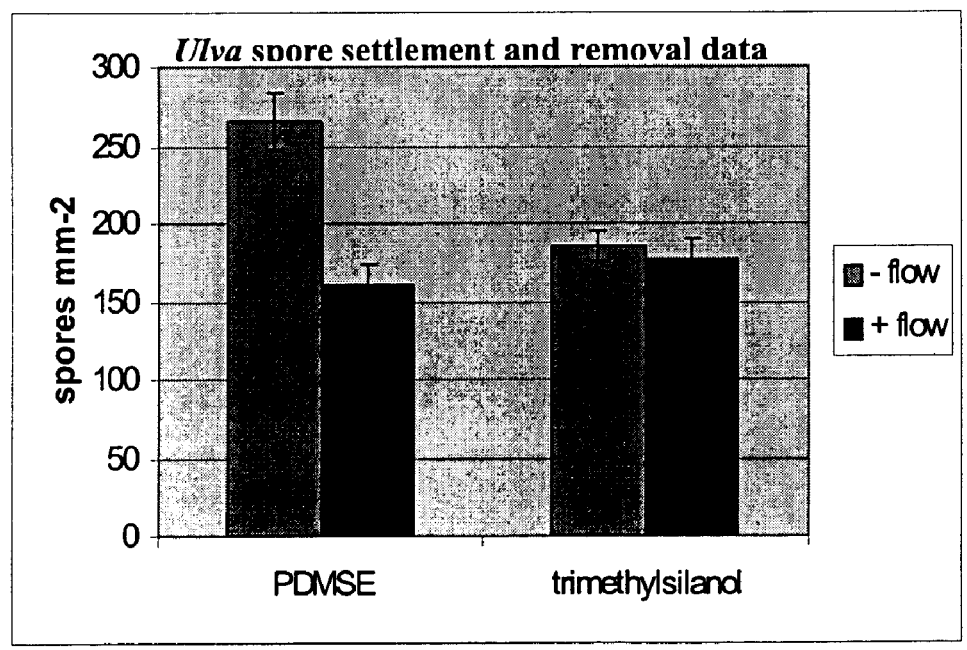
FIG. 12 shows data demonstrating less settlement on the trimethylsilanol comprising sample as compared to the reference polydimethylsiloxane (PDMS) elastomer composite sample.

FIG. 12 shows data demonstrating less settlement on the trimethylsilanol comprising sample according to the invention as compared to the reference PDMS sample. This was expected due to the chemical effect provide by the trimethylsilanol which is believed to lyse spores. A significant portion of the settled spores were released from the PDMS sample by applying hydrostatic pressure. Specifically, approximately 40% removal of settled spores in the flow channel from the applied shear stress for the standard PDMS was observed, but no significant spore removal from the sample having added trimethylsilanol was observed.

It should be understood that the Examples and embodiments described herein are for illustrative purposes only and that various modifications or changes in light thereof will be suggested to persons skilled in the art and are to be included within the spirit and purview of this application. The invention can take other specific forms without departing from the spirit or essential attributes thereof.

We claim:

1. A method of destroying target microorganisms, comprising the step of:
   contacting at least one target microorganism with at least one silanol end group containing molecule, wherein said silanol containing molecule comprises at least one selected from the group consisting of silanols ($R_1R_2R_3$SiOH), siloxanediols HO($R_1R_2$SiO)$_n$H and siloxanols HO($R_1R_2$SiO)nSiR$_1$R$_2$R$_3$, where $R_1$, $R_2$ and $R_3$ are selected from 1 to 4 carbon alkyl or fluoroalkyl moieties, or vinyl, or aryl groups and n is <6.

2. The method of claim 1, wherein said silanol containing molecule comprises at least one selected from the group consisting of triethylsilanol, diphenylmethylsilanol, t-butyldimethylsilanol, n-butyldimethylsilanol, n-propyldimethylsilanol, ethyldimethylsilanol, vinylphenylmethylsilanol, phenyldimethylsilanol, 3,3,3 trifluoro propyldimethylsilanol, benzyldimethylsilanol and phenethyldimethylsilanol, or mixtures thereof.

3. The method of claim 1, wherein said silanol containing molecule is disposed in an aqueous solution.

4. The method of claim 3, wherein said solution includes at least one ether.

5. The method of claim 4, wherein said ether comprises propylene glycol n-propyl ether.

6. The method of claim 1, wherein said silanol containing molecule comprises triethylsilanol.

7. The method of claim 6, wherein said triethylsilanol is disposed in an aqueous solution including propylene glycol n-propyl ether.

8. The method of claim 1, wherein said contacting step comprising flowing a carrier gas through a solution comprising said silanol containing molecule to form an aerosol, and directing said aerosol towards said surface.

9. The method of claim 1, wherein said silanol containing molecule is blended with a hydroxy containing polymer.

10. The method of claim 9, wherein said hydroxy containing polymer comprises a siloxane.

11. The method of claim 1, wherein said silanol containing molecule is a fragrant silanol, said fragrant silanol selected from $Ar(CH_2)_a R_1 R_2 SiOH$, where Ar is any phenyl or substituted phenyl group such that the substitution has a molecular weight of <60, a is <5, and $R_1$ and $R_2$ are Ar or alkyl or fluoro alkyl group with less than 4 carbons.

12. The method of claim 11, wherein said fragrant silanol is phenethyldimethylsilanol or benzyldimethylsilanol.

13. A composition of matter, comprising:
a silanol end group containing molecule blended with a polymer or in aqueous solution along with an ether-based cosolvent, wherein said silanol end group containing molecule is selected from the group consisting of silanols ($R_1 R_2 R_3 SiOH$), siloxanediols $HO(R_1 R_2 SiO)nH$ and siloxanols $HO(R_1 R_2 SiO)nSiR_1 R_2 R_3$, where $R_1$, $R_2$ and $R_3$ are selected from 1 to 4 carbon alkyl or fluoroalkyl moieties, or vinyl, or aryl groups and n is <6.

14. The composition of claim 13, wherein said silanol containing molecule comprises at least one selected from the group consisting of triethylsilanol, diphenylmethylsilanol, t-butyldimethylsilanol, n-butyldimethylsilanol, n-propyldimethylsilanol, ethyldimethylsilanol, vinylphenylmethylsilanol, phenyldimethylsilanol, 3,3,3 trifluoro propyldimethylsilanol, benzyldimethylsilanol and phenethyldimethylsilanol, or mixtures thereof.

15. The composition of claim 13, wherein said silanol containing molecule is dissolved in said aqueous solution along with a propylene glycol ether cosolvent.

16. The composition of claim 15, wherein said propylene glycol ether comprises propylene glycol n-propyl ether.

17. The composition of claim 13, wherein said silanol containing molecule comprises triethylsilanol.

18. The composition of claim 13, wherein said polymer is a hydroxy containing polymer.

19. The composition of claim 18, wherein said hydroxy containing polymer comprises a siloxane.

* * * * *